United States Patent [19]

Marshall et al.

[11] Patent Number: 5,342,922

[45] Date of Patent: Aug. 30, 1994

[54] INHIBITORS OF RETROVIRAL PROTEASE

[75] Inventors: Garland R. Marshall; Mihaly V. Toth, both of Clayton, Mo.

[73] Assignee: Washington University, St. Louis, Mo.

[21] Appl. No.: 320,742

[22] Filed: Mar. 8, 1989

[51] Int. Cl.$^5$ .................. C07K 7/06; A61K 37/02
[52] U.S. Cl. .................................................. 530/329
[58] Field of Search ........................... 530/329; 514/17

[56] References Cited

FOREIGN PATENT DOCUMENTS 301570 2/1989 European Pat. Off. ...... A61K 37/02

OTHER PUBLICATIONS

Schneider, et al. Cell, vol. 54, pp. 363–368, 1988.
Rich, "Inhibitors of aspartic proteinases," Barrett and Salvesen, eds., Elsevier Sci Publ. 1987, pp. 179–287.
Pearl, et al, "Sequence specificify of retroviral protease", Nature 326, 482 (1987).
Billich et al, "Synthetic Peptides as Substrates and Inhibitors of Human Immune Deficiency Virus—I Protease," J. Biol. Chem. 263, 17905–17908, 1988.
Korant et al., J. Cell. Biochem. 32, 91–95 (1986).
Katoh et al., Nature 329, 654–656 (1987).
Krausslick et al., J. Virology 62, 4393–4397 (1988).
Nutt et al., Proc. Natl. Acad. Sci. USA 85, 7179–7233(1988).
Seelmeier et al., Proc. Natl. Acad. Sci. USA 85, 6612–6616 (1985).
Kohl et al., Proc. Natl. Acad. Sci. USA 85, 4686–4690 (1988).
Darke et al., Biochem. Biophys. Res. Commun. 156, 297–303 (1988).
Kotler et al., Proc. Natl. Acad. Sci. USA 85, 4185–4189 (1988).
Sasaki et al., J. Med. Chem. 30, 1162–1166 (1987).
Toh et al., Nature 315, 691 (1985).

*Primary Examiner*—Merrell C. Cashion, Jr.
*Assistant Examiner*—S. G. Marshall
*Attorney, Agent, or Firm*—Scott J. Meyer

[57] ABSTRACT

Novel inhibitors of retroviral protease, e.g., HIV protease, are provided which are peptides having from about 4 to about 8 amino acid residues and which are substrates for said protease derived from known cleavage sites and modified to contain an internal $CH_2NH$ bond isostere.

2 Claims, No Drawings

INHIBITORS OF RETROVIRAL PROTEASE

BACKGROUND OF THE INVENTION

This invention relates to novel inhibitors of retroviral protease. More particularly, the invention is concerned with reduced amide bond modified peptide inhibitors of retroviral protease such as human immunodeficiency virus (HIV) protease. As such, these inhibitors have potential use for the treatment of acquired immune deficiency syndrome (AIDS) and aids related complex (ARC).

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names. It is the third known T-lymphocyte virus (HTLV-III) and has the capacity to replicate within cells of the immune system and thereby lead to a profound destruction of T4+ T-cells (or CD4+ cells). See, e.g., Gallo et al., *Science* 224, 500–503 (1984), and Popovic et al., *Ibid.*, 497–500 (1984). This retrovirus has been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [*Ann. Virol. Inst. Pasteur* 135 E, 119–134 (1984)], while HIV-2 was more recently isolated by Montagnier and his co-workers in 1986 [*Nature* 326, 662 (1987)]. As used herein HIV is meant to refer to these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, for example, Koff and Hoth, *Science* 241, 426–432 (1988).

The first drug to be approved by the U.S. Food and Drug Administration (FDA) for treatment of AIDS was zidovudine, better known under its former name, azidothymidine (AZT). Chemically, this drug is 3'-azido-3'-deoxythymidine. This drug was originally selected as a potential weapon against AIDS because it was shown to inhibit replicaton of the virus in vitro. Such in vitro tests are useful and virtually the only practical method of initially screening and testing potential anti-AIDS drugs. A serious drawback of AZT, however, is its toxic side-effects. Thus, the search for better anti-AIDS drugs continues.

Another approach being investigated recently for potential use in the treatment of AIDS is the development of synthetic peptides as inhibitors of retrovial protease. Thus, it is known that retroviruses, including the human immunodeficiency virus (HIV), express their genetic content by directing the synthesis of a polyprotein by the host. This precursor is then processed by proteolysis to give essential viral enzymes and structural proteins. A vitally encoded enzyme, the retroviral protease, is contained within the polyprotein and is responsible for the specific cleavages of the polyprotein yielding mature vital proteins. See, for example, Krausslich and Wimmer, *Ann. Rev. Biochem.* 57, 701–754 (1988).

Inhibition of the HIV protease as a means of therapeutic intervention in the treatment of AIDS and ARC patients is a logical strategy. Inhibition of virally encoded proteases as an approach to antiviral therapy has been demonstrated by Korant et al., *J. Cell. Biochem.* 32, 91–95 (1986), who showed that an endogenous inhibitor of cysteine proteases, cystatin, inhibited replication of poliovirus in tissue culture. A number of observations in the last few years serve to rationalize this approach for HIV. Isolation and sequence analysis of the HIV-1 [Ratner et al., *Nature* 313, 277–284 (1985)] and HIV-2 [Guyader et al., *Nature* 326, 662–669 (1987)] viral genomes show homology of a segment [Toh et al., *Science* 231, 1567 (1986)] with other retroviral proteases [Yasumaga et al., *FEBS Lett.* 199, 145 1986)] which show limited homology with a known class of proteolytic enzyme, the aspartic proteinases [Rich, "Inhibitors of aspartic proteinases" in *Proteinase Inhibitors*, Barrett and Salvesen, eds., Elsevier Science Publ., Amsterdam, 1987, pp. 179–217]. This includes the presence of a conserved Asp-Thr-Gly sequence characteristic of the active site of aspartic proteinases. Known inhibitors of this class of enzyme (pepstatin at high concentration and DAN) inhibit the protease activity of avian myeloblastosis virus [Dittmar and Moelling, *J. Virology* 28, 106 (1978)], bovine leukemia, Maloney murine leukemia and human T-cell leukemia viruses as shown by Dittmar and Moelling, supra, and by Katoh et al., supra. Several groups [Hansen et al., *J. Virology* 62, 1785–1791 (1988) and Krausslich et ai., *Ibid.* 62, 4393–4397 (1988)] have demonstrated inhibition by pepstatin of processing of gag-pol polyprotein by HIV protease. Nutt et al., *Proc. Natl. Acad. Sci. USA* 85, 7179–7233 (1988), reported that pepstatin inhibited synthetic HIV protease with a $K_i = 1.4$ $\mu$molar. This link to aspartic proteinases presents the opportunity to draw upon the knowledge-base gathered on renin, the most prominent aspartic proteinase, to expedite the development of specific and potent inhibitors of HIV proteases.

The HIV protease has been shown to be essential in the maturation of viral proteins necessary for viral multiplication such as the gag core proteins when expressed in yeast [Kramer et al., *Science* 231, 1580 (1986)] or the reverse transcriptase (RT) when expressed in *E. coli* [Farmerie et al., *Science* 263, 305 (1987)]. Modification by Seelmeier et al., *Proc. Natl. Acad. Sci. USA* 85, 6612–6616 (1988), and by Mous et al., *J. Virology* 62, 1433–1436 (1988), of the aspartic residue (Asp-25) corresponding by sequence homology to the active site residue by site-directed mutagenesis prevents processing of the polyprotein. Kohl et al., *Proc. Natl. Acad. Sci. USA* 85, 4686–4690 (1988), have also shown in an *E. coli* expression system that the replacement of Asp-25 with Asn in HIV protease prevents cleavage of gag p55 in cultured cells and inhibits infectivity in tissue culture. Loeb et al., *J. Virology* 63, In Press, 1988, have carried out an extensive mutagenesis study on HIV protease expressed in *E. coli* and shown inhibition of gag processing by both conservative and non-conservative mutation of the amino acids adjacent to the assumed active site. This demonstrates in HIV a similar role for the protease to that shown by Katoh et al., *Virology* 145, 280–292 (1985), for Maloney murine leukemia virus where deletions in the protease region led to immature virus particles with markedly reduced infectivity.

Modification of known substrate sequences is an accepted approach to inhibitor generation. HIV protease cleaves the virally encoded polyprotein at several sites to liberate the gag proteins (p17,p24,p15) as well as the protease (Prot) itself and reverse transcriptase (p66). Thus, small peptides overlapping each of the cleavage sites (p17/p24, p24/p15, p15/Prot, and Prot/p66) become candidates for modification. Schneider and Kent, *Cell* 54 363 (1988), have prepared peptide substrates of twenty or more residues corresponding to each of these cleavage sites and demonstrated that their synthetic enzyme cleaved at the appropriate site. Darke et al., *Biochem. Biophys. Res. Commun.* 156, 297–303 (1988), showed that both expressed and synthetic enzyme cleaved at the proposed processing sites with larger synthetic peptides. Cleavage of VSQNYPIV, corresponding to the cleavage site between gag p17 and gag p24, occurred at the same rate as a fifteen residue substrate with a $K_m$=2.5 mM. The minimal length peptide substrate that was shown to be cleaved (at 90% of the rate of the octapeptide) was a heptapeptide, SQNYPIV. Either SQNY-PI, QNY-PIV, or acetyl-QNY-PIV failed to be cleaved. In studies on the protease from the retrovirus, avian sarcoma-leukosis virus (ASLV), Kotler et al, *Proc. Natl. Acad. Sci. USA* 85, 4185–4189 (1988), examined decapeptide substrates and suggest that the minimal size for cleavage with ASLV protease is longer than six residues. An unspecified hexapeptide corresponding to a sequence of HIV containing a Tyr-Pro cleavage site was reported to be a relatively poor substrate and act as an inhibitor of the cleavage of better substrates of ASLV protease.

DESCRIPTION OF THE INVENTION

In accordance with the present invention, novel inhibitors of retroviral protease are provided. These inhibitors are reduced amide bond modified peptides of relatively short amino acid chain length of from about 4 to about 8 amino acid residues, and preferably are hexapeptides and heptapeptides. These inhibitors contain a reduced internal amide bond, namely the $CH_2NH$ bond isostere. The preferred peptide inhibitors are based on substrates for HIV protease derived from HIV-1 and HIV-2 known cleavage sites and modified to contain the $CH_2NH$ bond isostere. In the case of attachment to proline, the isostere will be the equivalent $CH_2N$.

The following illustrate the preferred peptide inhibitors of HIV protease. The corresponding cleavage site from which these inhibitors were derived is indicated.

| Cleavage Site | Peptide |
|---|---|
| p17/p24 | Ac—Gln—Asn—Tyr-ψ[$CH_2N$]—Pro—Ile—Val—$NH_2$ |
| (HIV2) | Ac—Gly—Asn—Tyr-ψ[$CH_2N$]—Pro—Val—Gln—$NH_2$ |
| p24/p15 | Ac—Thr—Ile—Met-ψ[$CH_2NH$]—Met—Gln—Arg—$NH_2$ |
| | Ac—Thr—Ile—Nle-ψ[$CH_2NH$]—Nle—Gln—Arg—$NH_2$ |
| | Ac—Thr—Ile—Leu-ψ[$CH_2NH$]—Leu—Gln—Arg—$NH_2$ |
| | Ac—Thr—Ile—Nle-ψ[$CH_2NH$]—Leu—Gln—Arg—$NH_2$ |
| | Ac—Thr—Ile—Nle-ψ[$CH_2NH$]—Cha—Gln—Arg—$NH_2$ |
| | Ac—Thr—Ile—Nle-ψ[$CH_2NH$]—Phe—Gln—Arg—$NH_2$ |
| | Ac—Thr—Ile—Nle-ψ[$CH_2NH$]—Cle—Gln—Arg—$NH_2$ |
| | Ac—Thr—Ile—Nle-ψ[$CH_2NH$]—MeNle—Gln—Arg—$NH_2$ |
| | Ac—Thr—Ile—Nle-ψ[$CH_2NH$]—Nle—Gln—D—Arg—$NH_2$ |
| | Ac—Thr—Ile—Nle-ψ[$CH_2NH$]—Ile—Gln—Arg—$NH_2$ |
| | Ac—D—Thr—Ile—Nle-ψ[$CH_2NH$]—Nle—Gln—Arg—$NH_2$ |
| | Ac—Thr—Ile—Nle-ψ[$CH_2NH$]—Nle—Gln—Nva—$NH_2$ |
| | Ac—Arg—Gln—Nle-ψ[$CH_2NH$]—Nle—Ile—Thr—$NH_2$ |
| | Ac—Thr—Ile—Nle-ψ[$CH_2NH$]—Nle—Gln—$NH_2$ |
| | Ac—Ile—Nle-ψ[$CH_2NH$]—Nle—Gln—Arg—$NH_2$ |
| p15/Prot | Ac—Phe—Asn—Phe-ψ[$CH_2N$]—Pro—Gln—Ile—$NH_2$ |
| | Ac—Ser—Phe—Asn—Phe-ψ[$CH_2N$]—Pro—Gln—Ile—$NH_2$ |
| (HIV2) | Ac—Leu—Ala—Ala-ψ[$CH_2N$]—Pro—Gln—Phe—$NH_2$ |
| Prot/p66 | Ac—Leu—Asn—Phe-ψ[$CH_2N$]—Pro—Ile—Ser—OH |
| | $H_2N$—Thr—Leu—Asn—Phe-ψ[$CH_2N$]—Pro—Ile—Ser—OH |
| (HIV2) | Ac—Leu—Asn—Leu-ψ[$CH_2N$]—Pro—Val—Ala—$NH_2$ |
| | $H_2N$—Ser—Leu—Asn—Leu-ψ[$CH_2N$]—Pro—Val—Ala—OH |

The novel inhibitors of HIV protease and other such retroviral proteases can be prepared by known solution and solid phase peptide synthesis methods. For introducing the $CH_2NH$ bond isostere, the solid phase synthesis method of Sasaki et al., *J. Med. Chem.* 30, 1162–1166, (1987), is suitable. This method employs a combination of sodium cyanoborohydride mediated reductive alkylation of resin-bound peptide amine with a tert-butoxycarbonyl amino acid aldehyde for introduction of a $CH_2NH$ bond and conventional solid-phase peptide chemistry.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxypthalimide or N-hydroxy-succinimide, and the various cleavage reagents, e.g., trifluoroacetic acid, HCL in dioxane, boron tris-(trifluoracetate) and cyanogen bromide, and reaction in solution with isolation and purification of intermediates is well-known classical peptide methodology.

The preferred peptide synthesis method follows conventional Merrifield solid-phase procedures. See Merrifield, *J. Amer. Chem. Soc.* 85, 2149–54 (1963) and *Science* 150, 178–85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or p-methylbenzhydrylamine polymer. This method conveniently simplifies the number of procedural manipulations since removal of the excess reagents at each step is effected simply by washing the polymer.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology* 32, pp. 221-296, F. F. Nold, Ed., Interscience Publishers, New York, 1969; and Erickson and Merrifield, *The Proteins*, Vol. 2, p. 255 et seq. (ed. Neurath and Hill), Academic Press, New York, 1976.

In order to illustrate specific preferred embodiments of the invention in greater detail, the following exemplary laboratory preparative work was carried out.

EXAMPLE

Solid Phase Synthesis of HIV Proteases, Substrates and Inhibitors

Acetyl hexapeptide amides with and without reduced internal amide bonds were prepared by solid phase peptide synthesis using the p-methylbenzhydrylamine polymer. For each synthesis, 0.5 grams of polymer was used (0.5 mmole). The following synthetic protocol was used for incorporation of the Boc-amino acids:

---

Deprotection: 50% trifluoroacetic acid/CH$_2$Cl$_2$ 5 min and 25 min
    CH$_2$Cl$_2$      2 × 1 min
    Isopropanol      2 × 1 min
    CH$_2$Cl$_2$      2 × 1 min
Neutralization: 10% diisopropylethylamine/CH$_2$Cl$_2$ 3 min and 5 min
    CH$_2$Cl$_2$      2 × 1 min
    DMF      2 × 1 min
Coupling: 4 equivalent of Boc-amino acid and 4 equiv. of diisopropylcarbodiimide in the presence of 4 equiv. of hydroxybenzotriazole in DMF for 2 hours. A repeated coupling in DMF was performed if the Kaiser test was positive.

---

The dipeptide reduced peptide bond analogs were prepared either in solution and incorporated as a unit in the solid phase protocol, or prepared in situ by reductive alkylation. 4 equiv. of Boc-amino acid aldehyde (Boc-AA-al) prepared by the procedure of Fehrentz and Castro, *Synthesis* 1983, 676–679, in DMF containing 1% acetic acid was reacted with the trifluoroacetate salt (Tfa) of the peptide amine followed by reduction with 4 equiv. NaCNBH$_3$ in portions according to Sasaki et al., *J. Med. Chem.* 30, 1162–1166 (1987). Coupling was repeated with 2 equiv. alkylating reagent. In the case of Leu-Pro and Phe-Pro, reduced dipeptide units were prepared. Boc-Leu-al was reacted with Tfa·Pro-OH in methanol containing 1% acetic acid and reduced by NaCNBH$_3$. Boc-Leu-Ψ[CH$_2$N]-Pro-OH was isolated using flash chromatography (EtoAc/MeOH, 1:3). Boc-Phe-al was coupled to Pro-OBzl and reduced as above. Boc-Phe-Ψ[CH$_2$N]-Pro-OBzl was isolated and the benzyl ester removed by catalytic hydrogenation. Completed peptides were cleaved by the high HF/anisole, 9:1 procedure of Tam et al., *J. Amer. Chem. Soc.* 105, 6442-6455 (1983). For peptides containing methionine, dimethylsulfide and ethanedithiol were used as scavengers. Crude peptides were dissolved in 20% acetic acid and lyophilized. They were purified by reversed-phase HPLC on a C18 semipreparative column using a 0.1% TFA and acetonitrile gradient. Their identity was confirmed by high-resolution mass spectrometry, NMR and amino acid analyses.

HIV Protease Assay

The HIV protease assay was conducted using either synthetic HIV protease [Schneider and Kent, *Cell* 54, 363 (1988)] kindly supplied by Dr. StephenKent of Caltech, or cloned material expressed in *E. coli* supplied by Dr. George Glover of the Monsanto Company. In all cases examined, the cleavage patterns and inhibition results were identical. Synthetic protease (1 mg/ml) was dissolved in a buffer (20 mM PIPES, 0.5%NP-40 detergent, 1 mM dithiothreitol), pH 6.5. Substrates were also dissolved in the same buffer at 1 mg/ml concentration. 5 μl of substrate and 5 μl of HIV protease were added to an Eppendorf tube which was centrifuged for one minute and incubated at 25° for the desired time. The reaction was stopped by the addition of 50 μl of 50% TFA. The sample was diluted with 200 μl of water and applied to a C$_4$ HPLC column developed with 0.1% TFA for 5 min followed by a gradient of 0–50% acetonitrile in 50 min. For inhibitor studies, 5 μl of the protease solution was preincubated for 10 min with the 5 μl of inhibitor (dissolved in 10% DMSO and diluted to 1 mg/ml with buffer). Then 5 μl of test substrate, acetyl-Thr-Ile-Met-Met-Gln-Arg-NH$_2$ was added in order to determine inhibition of cleavage. Reactions were stopped as above and cleavage rates were monitored by HPLC as above.

Substrate analogs were prepared in order to examine the relative hydrolysis rates of the various sites. As an objective was the development of potential therapeutic agents, a minimal size for recognition was desired as illustrated by hepta- and hexapeptide substrates (Table 1). In contrast to the reports of Darke et al., supra, and Kotler et al., supra, hexapeptides were found to function as good substrates provided that their charged amino and carboxyl termini are blocked such as, for example, with acetyl and amide groups, respectively, although this is not essential to activity. The p24/p15 hexapeptide Ac-Thr-Ile-Met-Met-Gln-Arg-NH$_2$, was characterized with a K$_m$=1.4 mM and a V$_{max}$=725 nmoles/min/mg. This compares favorably with the data of Darke et al., supra, for most of the longer peptide substrates. Relative cleavage rates were measured by comparing the percent of a standard substrate concentration cleaved by the same concentration of enzyme in twenty minutes (linear portion of curve).

TABLE 1

| | Substrates for HIV protease derived from HIV-1 or HIV-2 known cleavage sites. | |
|---|---|---|
| Cleavage Site | Peptide | Relative Rate |
| p17/24 | Ac—Gln—Asn—Tyr—Pro—Ile—Val—NH$_2$ | 0.04 |
| (HIV2) | Ac—Gly—Asn—Tyr—Pro—Val—Gln—NH$_2$ | — |
| p24/p15 | Ac—Thr—Ile—Met—Met—Gln—Arg—NH$_2$ | 1.00* |
| | Ac—Thr—Ile—Nle—Hle—Gln—Arg—NH$_2$ | 0.95 |
| | Ac—Thr—Ile—PnF—Nle—Gln—Arg—NH$_2$ | — |
| | Ac—Thr—Ile—Nle—PnF—Gln—Arg—NH$_2$ | 0.57 |
| | Aba—Thr—Ile—Nle—PnF—Gln—Arg—NH$_2$ | 1.46 |
| p15/Prot | Ac—Phe—Asn—Phe—Pro—Gln—Ile—NH$_2$ | — |

TABLE 1-continued

Substrates for HIV protease derived
from HIV-1 or HIV-2 known cleavage sites.

| Cleavage Site | Peptide | Relative Rate |
|---|---|---|
|  | Ac—Ser—Phe—Asn—Phe—Pro—Gln—Ile—NH$_2$ | — |
| (HIV2) | Ac—Leu—Ala—Ala—Pro—Gln—Phe—NH$_2$ | — |
| Prot/p66 | Ac—Leu—Asn—Phe—Pro—Ile—Ser—OH | — |
| (HIV2) | Ac—Leu—Asn—Leu—Pro—Val—Ala—NH$_2$ | — |

*This peptide used as control to determine relative rate of the other peptides.

Reduced dipeptide analogs were prepared both in solution prior to incorporation by solid phase peptide synthesis, and in situ during solid-phase synthesis according to Sasaki et al., supra, by addition of the Boc-amino acid aldehyde to the amino terminal of the peptide chain and reduction of the Schiff's base adduct. As it was desired to fully characterize the reaction with the secondary amine of Pro before utilizing the approach of Sasaki et al., the dipeptide analogs, Boc-Leu-Ψ[CH$_2$N]-Pro-OH and Boc-Phe-Ψ[CH$_2$N]-Pro-OBzl, were prepared and characterized. Removal of the C-terminal benzyl protecting group by catalytic hydrogenation gave an appropriate compound for incorporation into substrate sequences by solid-phase synthesis. These dipeptides were incorporated into the two substrate heptapeptide sequences from the retroviral gag-polyproteins of HIV which were cleaved to yield the major core gag protein as follows:

Prot/p66

Thr-Leu-Asn-Phe-Ψ[CH$_2$N]-Pro-Ile-Ser      HIV-1

Ser-Leu-Asn-Leu-Ψ[CH$_2$N]-Pro-Val-Ala.      HIV-2

These analogs were assayed in solution for their ability to inhibit crude extract of E. coli with retroviral protease (HIV-1) activity demonstrated with synthetic substrates. In preliminary tests, both appeared inactive, but the assay was compromised by E. coli enzymes and the presence of the free carboxyl and amino groups. A reduced amide analog was prepared using the procedure of Sasaki et al., supra, with the structure, Ac-Gly-Asn-Tyr-Ψ[CH$_2$NH]-Pro-Val-Gln-NH$_2$. When tested against the synthetic HIV-1 protease prepared by Schneider and Kent, supra, inhibition was clearly seen with an affinity approximately five-fold greater than the best substrate, Ac-Thr-Ile-Met-Met-Gln-Arg-NH$_2$. The two heptapeptides above also showed good inhibition when tested against the synthetic enzyme. The lack of activity in crude extracts may reflect metabolism of the inhibitors by E. coli exopeptidases. Ac-Thr-Ile-Met-Ψ[CH$_2$NH]-Met-Gln-Arg-HN$_2$ was then prepared and also showed enhanced affinity. The reduced amide transition state inhibitor yielded inhibitors in all four substrate sequences to which it has been applied (Table 2).

Table 2, below, also shows the in vitro inhibition assay results for illustrative inhibitors of the invention. Under these assay conditions, pepstatin A had a K$_I$=5.46 μM. The compounds whose affinities have not been fully characterized are classified into four categories based on comparative inhibition studies. +++ = submicromolar, ++ = 1–100 micromolar, + = greater than 100 micromolar, − = inactive. NE = affinity not estimated.

TABLE 2

Reduced amide bond inhibitors of HIV protease.

| Cleavage Site | Peptide | K$_I$ |
|---|---|---|
| p17/p24 | Ac—Gln—Asn—Tyr-Ψ[CH$_2$N]—Pro—Ile—Val—NH$_2$ | 17.2 μM |
| (HIV2) | Ac—Gly—Asn—Tyr-Ψ[CH$_2$N]—Pro—Val—Gln—NH$_2$ | ++ |
| p24/p15 | Ac—Thr—Ile—Met-Ψ[CH$_2$NH]—Met—Gln—Arg—NH$_2$ | +++ |
|  | Ac—Thr—Ile—Nle-Ψ[CH$_2$NH]—Nle—Gln—Arg—NH$_2$ | 789 nM |
|  | Ac—Thr—Ile—Leu-Ψ[CH$_2$NH]—Leu—Gln—Arg—NH$_2$ | 734 nM |
|  | Ac—Thr—Ile—Nle-Ψ[CH$_2$NH]—Leu—Gln—Arg—NH$_2$ | +++ |
|  | Ac—Thr—Ile—Nle-Ψ[CH$_2$NH]—Cha—Gln—Arg—NH$_2$ | +++ |
|  | Ac—Thr—Ile—Nle-Ψ[CH$_2$NH]—Phe—Gln—Arg—NH$_2$ | +++ |
|  | Ac—Thr—Ile—Nle-Ψ[CH$_2$NH]—Cle—Gln—Arg—NH$_2$ | + |
|  | Ac—Thr—Ile—Nle-Ψ[CH$_2$NH]—MeNle—Gln—Arg—NH$_2$ | + |
|  | Ac—Thr—Ile—Nle-Ψ[CH$_2$NH]—Nle—Gln—D—Arg—NH$_2$ | ++ |
|  | Ac—Thr—Ile—Nle-Ψ[CH$_2$NH]—Ile—Gln—Arg—NH$_2$ | +++ |
|  | Ac—D—Thr—Ile—Nle-Ψ[CH$_2$NH]—Nle—Gln—Arg—NH$_2$ | ++ |
|  | Ac—Thr—Ile—Nle-Ψ[CH$_2$NH]—Nle—Gln—Nva—NH$_2$ | ++ |
|  | Ac—Arg—Gln—Nle-Ψ[CH$_2$NH]—Nle—Ile—Thr—NH$_2$ | ++ |
|  | Ac—Thr—Ile—Nle-Ψ[CH$_2$NH]—Nle—Gln—NH$_2$ | ++ |
|  | Ac—Ile—Nle-Ψ[CH$_2$NH]—Nle—Gln—Arg—NH$_2$ | ++ |
| p15/Prot | Ac—Phe—Asn—Phe-Ψ[CH$_2$N]—Pro—Gln—Ile—NH$_2$ | ++ |
|  | Ac—Ser—Phe—Asn—Phe-Ψ[CH$_2$N]—Pro—Gln—Ile—NH$_2$ | ++ |
| (HIV2) | Ac—Leu—Ala—Ala-Ψ[CH$_2$N]—Pro—Gln—Phe—NH$_2$ | + |
| Prot/p66 | Ac—Leu—Asn—Phe-Ψ[CH$_2$N]—Pro—Ile—Ser—OH | ++ |
|  | H$_2$N—Thr—Leu—Asn—Phe-Ψ[CH$_2$N]—Pro—Ile—Ser—OH | ++ |
| (HIV2) | Ac—Leu—Asn—Leu-Ψ[CH$_2$N]—Pro—Val—Ala—NH$_2$ | ++ |
|  | H$_2$N—Ser—Leu—Asn—Leu-Ψ[CH$_2$N]—Pro—Val—Ala—OH | 13.1 μM |

Preliminary studies evaluating three of these inhibitors (Ac-Gln-Asn-Tyr-Ψ[CH$_2$N]-Pro-Ile-Val-NH$_2$, Ac-Thr-Ile-Met-Ψ[CH$_2$NH]-Met-Gln-Arg-NH$_2$, and Ac-Thr-Ile-Nle--Ψ[CH$_2$NH]-Nle-Gln-Arg-NH$_2$) in acute HIV infection assays with CD4+ human lymphocyte cells (H9 cells) (2 ml cultures) showed dose-dependent anti-viral effects as measured by quantitation of p24 antigen (single time point after syncitia formation) with no apparent toxicity as measured by cell count.

Amino acids are shown herein either by standard one letter or three letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Other standard abbreviations used in the peptide sequences herein are:

Nle=norleucine,
Nva=norvaline,
MeNle=N-methyl-norleucine,
Aba=2-aminobenzoic acid,
Cha=cyclohexylalanine,
PnF=p-nitrophenylalanine,
Cle=1-aminocyclopentanecarboxylic acid, and
Ac=acetyl.

Various other examples will be apparent to the person skilled in the art after reading the present disclosure without departing from the spirit and scope of the invention. For example, various derivatives of the disclosed peptides having substantially similar antiviral activity can be readily made by appropriate substitutions during the peptide synthesis or by subsequent modification. It is intended that all such other examples be included within the scope of the appended claims.

What is claimed is:

1. An inhibitor of HIV protease of claim 1 selected from the group consisting of
Ac-Gln-Asn-Tyr-Ψ[CH$_2$N]-Pro-Ile-Val-NH$_2$,
Ac-Gly-Asn-Tyr-Ψ[CH$_2$N]-Pro-Val-Gln-NH$_2$, Ac-Thr-Ile-Met-Ψ[CH$_2$NH]-Met-Gln-Arg-NH$_2$,
Ac-Thr-Ile-Nle-Ψ[CH$_2$NH]-Nle-Gln-Arg-NH$_2$,
Ac-Thr-Ile-Leu-Ψ[CH$_2$NH]-Leu-Gln-Arg-NH2,
Ac-Thr-Ile-Nle-Ψ[CH$_2$NH]-Leu-Gln-Arg-NM$_2$,
Ac-Thr-Ile-Nle-Ψ[CH$_2$NH]-Cha-Gln-Arg-NH$_2$,
Ac-Thr-Ile-Nle-Ψ[CH$_2$NH]-Phe-Gln-Arg-NH$_2$,
Ac-Thr-Ile-Nle-Ψ[CH$_2$NH]-Cle-Gln-Arg-NH$_2$,
Ac-Thr-Ile-Nle-Ψ[CH$_2$NH]-MeNle-Gln-Arg-NH$_2$,
Ac-Thr-Ile-Nle-Ψ[CH$_2$NH]-Nle-Gln-D-Arg-NH$_2$,
Ac-Thr-Ile-Nle-Ψ[CH$_2$NH]-Ile-Gln-Arg-NH$_2$,
Ac-D-Thr-Ile-Nle-Ψ[CH$_2$NH]-Nle-Gln-Arg-NH$_2$,
Ac-Thr-Ile-Nle-Ψ[CH$_2$NH]-Nle-Gln-Nva-NH$_2$,
Ac-Arg-Gln-Nle-Ψ[CH$_2$NH]-Nle-Ile-Thr-NH$_2$,
Ac-Thr-Ile-Nle-Ψ[CH$_2$NH]-Nle-Gln-NH$_2$,
Ac-Ile-Nle-Ψ[CH$_2$NH]-Nle-Gln-Arg-NH$_2$, Ac-Phe-Asn-Phe-Ψ[CH$_2$N]-Pro-Gln-Ile-NH$_2$,
Ac-Ser-Phe-Asn-Phe-Ψ[CH$_2$N]-Pro-Gln-Ile-NH$_2$,
Ac-Leu-Ala-Ala-Ψ[CH$_2$N]-Pro-Gln-Phe-NH$_2$, Ac-Leu-Asn-Phe-Ψ[CH$_2$N]-Pro-Ile-Ser-OH,
H$_2$N-Thr-Leu-Asn-Phe-Ψ[CH$_2$N]-Pro-Ile-Ser-OH,
Ac-Leu-Asn-Leu-Ψ[CH$_2$N]-Pro-Val-Ala-NH$_2$, and
H$_2$N-Ser-Leu-Asn-Leu-Ψ[CH$_2$N]-Pro-Val-Ala-OH.

2. The inhibitor of claim 1 having the following structure:
Ac-Lue-Asn-Phe-Ψ[CH$_2$N]-Pro-Ile-Ser-OH.

* * * * *